United States Patent [19]
Erickson

[11] Patent Number: 5,876,382
[45] Date of Patent: Mar. 2, 1999

[54] SAFETY SYRINGE WITH RETRACTABLE NEEDLE HOLDER

[75] Inventor: Charles W. Erickson, Minneapolis, Minn.

[73] Assignee: UltiMed, Inc, St. Paul, Minn.

[21] Appl. No.: 663,835

[22] Filed: Jun. 14, 1996

[51] Int. Cl.⁶ ..................................................... A61M 5/32
[52] U.S. Cl. ........................... 604/198; 604/195; 604/110
[58] Field of Search ..................................... 604/110, 181, 604/187, 195, 198, 218, 228, 240–243

[56] References Cited

U.S. PATENT DOCUMENTS

| | | | |
|---|---|---|---|
| 553,370 | 7/1896 | Berger et al. | 604/110 |
| 4,921,486 | 5/1990 | DeChellis et al. | 604/110 |
| 4,955,869 | 9/1990 | Bin | 604/195 |
| 4,966,593 | 10/1990 | Lennox | 604/198 |
| 5,013,301 | 5/1991 | Marotta, Jr. et al. | 604/110 |
| 5,114,404 | 5/1992 | Paxton et al. | 604/110 |
| 5,114,410 | 5/1992 | Batlle | 604/195 |
| 5,205,823 | 4/1993 | Zdeb | 604/110 |
| 5,578,015 | 11/1996 | Robb | 604/195 |

Primary Examiner—Wynn Wood Coggins
Assistant Examiner—Deborah Blyveis
Attorney, Agent, or Firm—Roger W. Jensen

[57] ABSTRACT

A safety syringe having a cylindrical hollow barrel member of semi-elastic material has a seal and stop device at the distal open end and a first restraining stop device axially spaced a preselected distance from the distal open end. A cylindrically shaped needle carrier is initially positioned within the barrel member between the stop device, the needle carrier having a centrally located recess device at the proximal end thereof for receiving and holding a male piston extension device. A piston rod having a piston is provided for drawing fluid into the barrel and forcing fluid out of the barrel through a longitudinal bore in the needle carrier and through an elongated hollow needle attached to the needle carrier. The piston has a male extension at the distal end for engagement with the female recess of the needle carrier. The piston coacts with the first restraining stop device so as to stretch the barrel to disengage the stop means from the needle carrier and to permit subsequent longitudinal movement of the assembled and locked piston and needle carrier in the proximal direction relative to the barrel so as to withdraw the hollow needle means totally within the barrel to prevent accidental contact of the needle with an errant body part.

10 Claims, 4 Drawing Sheets

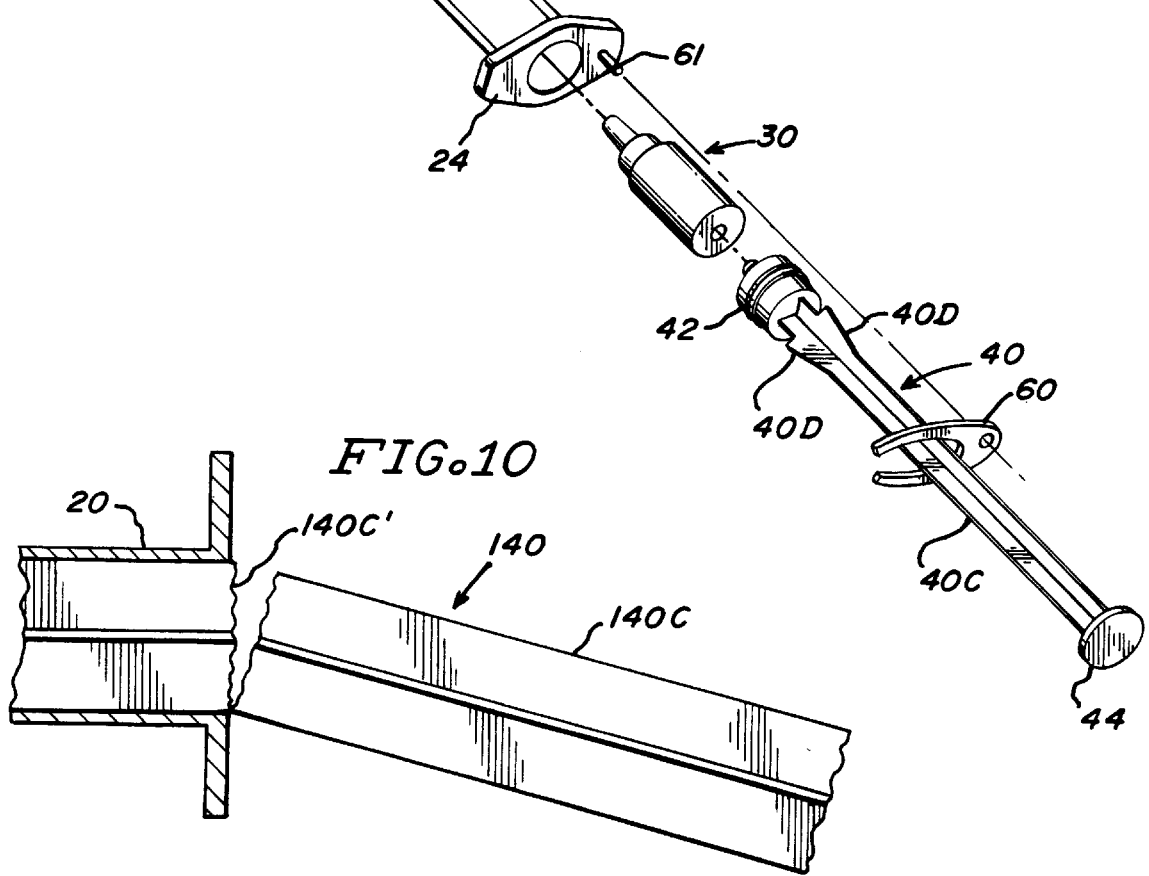

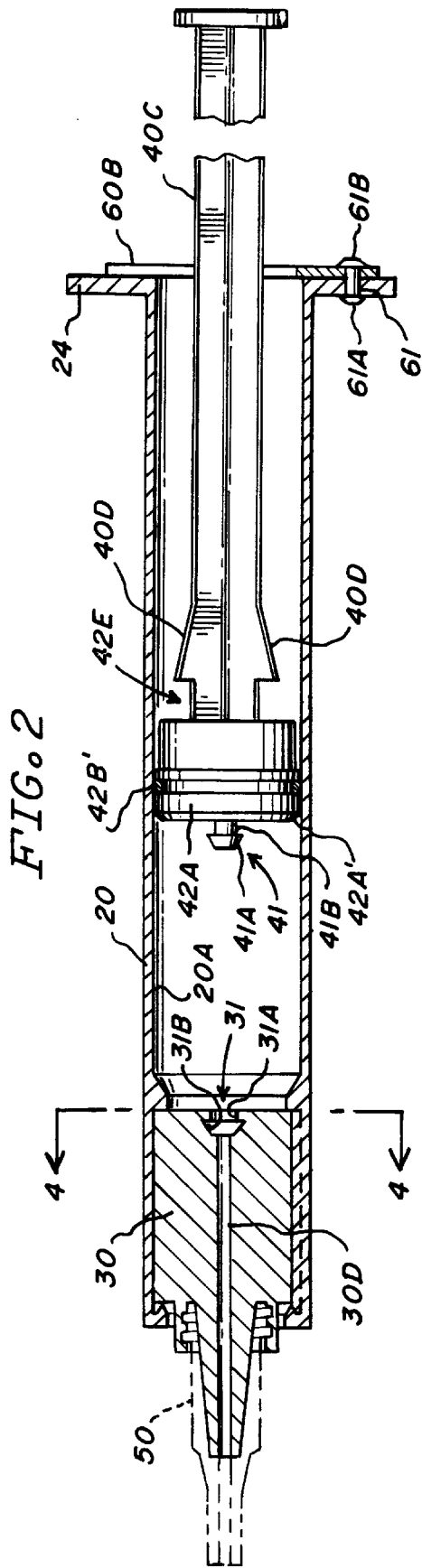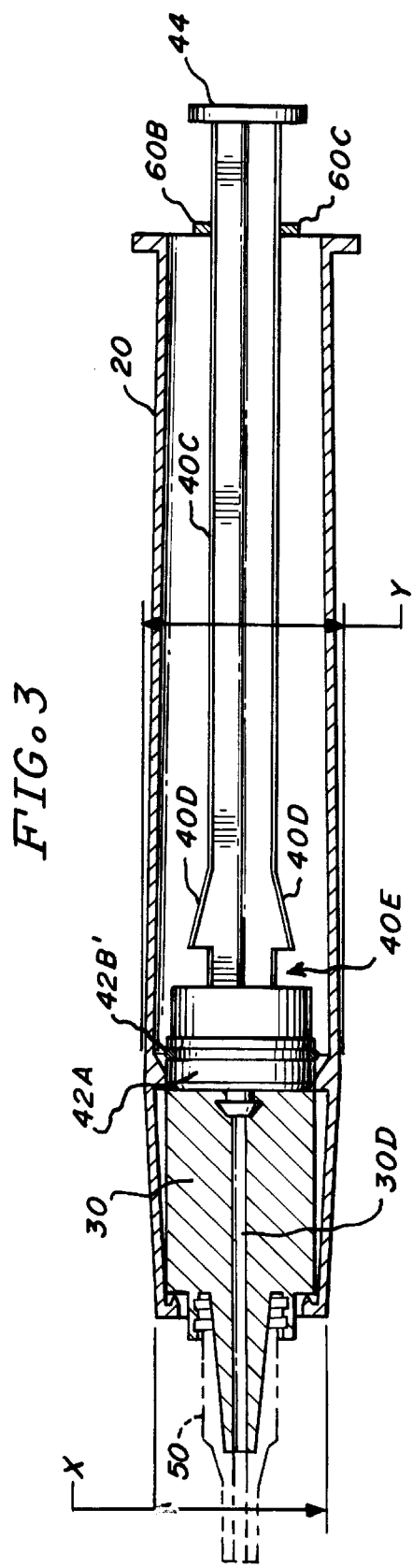

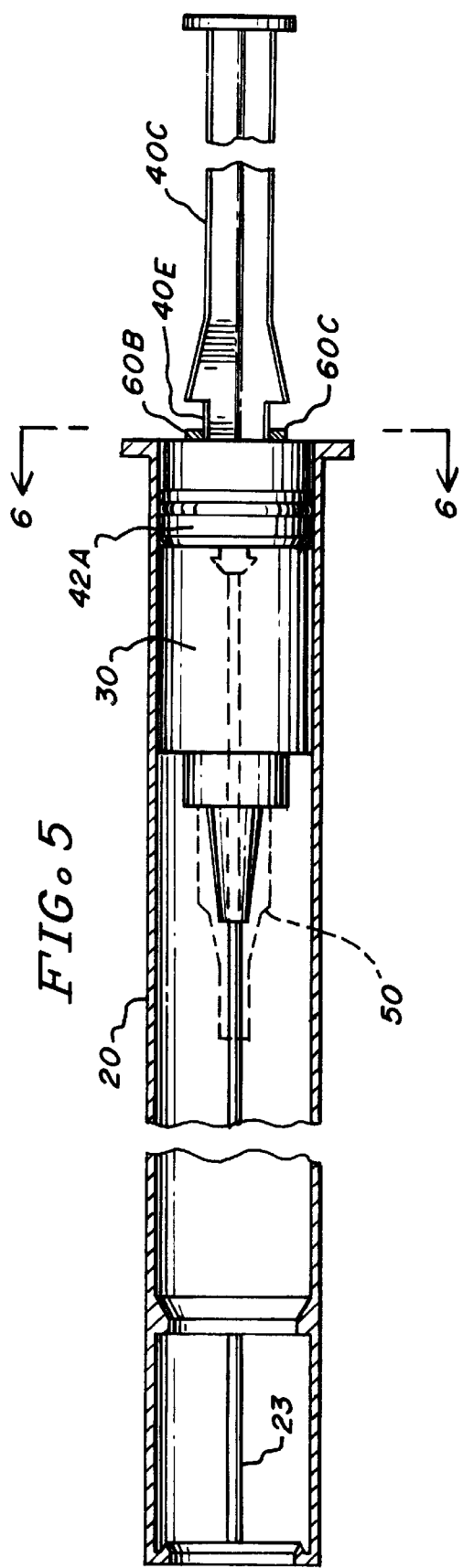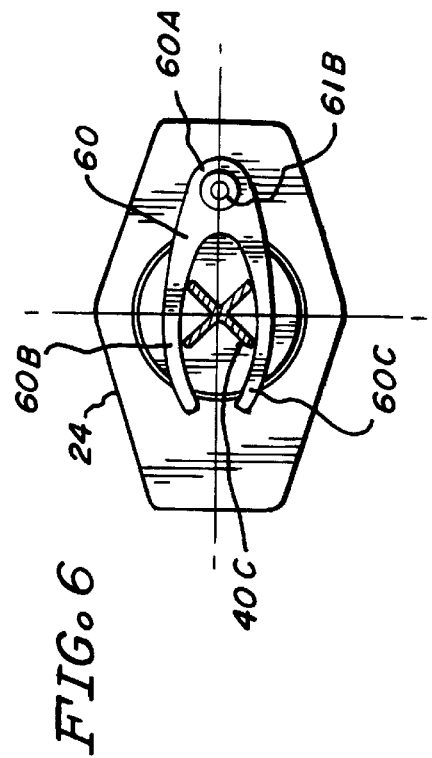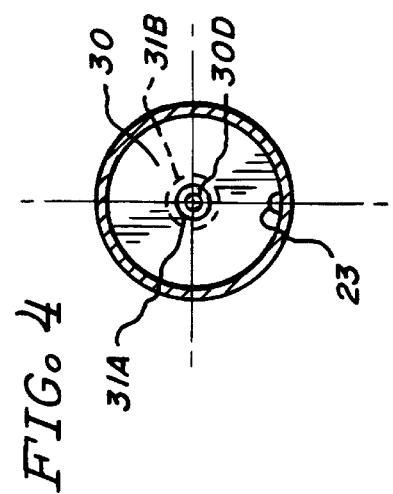

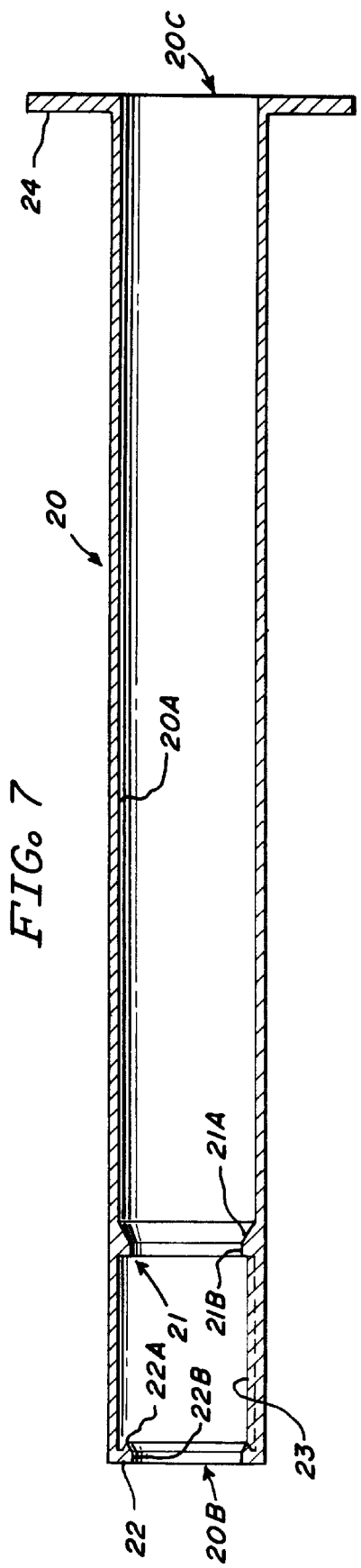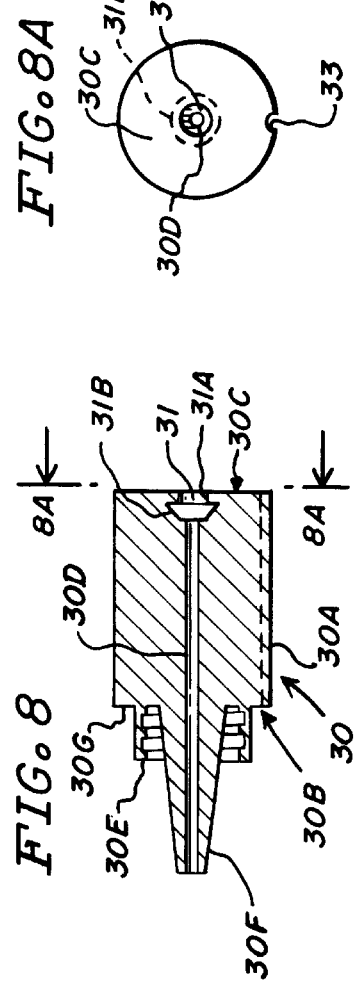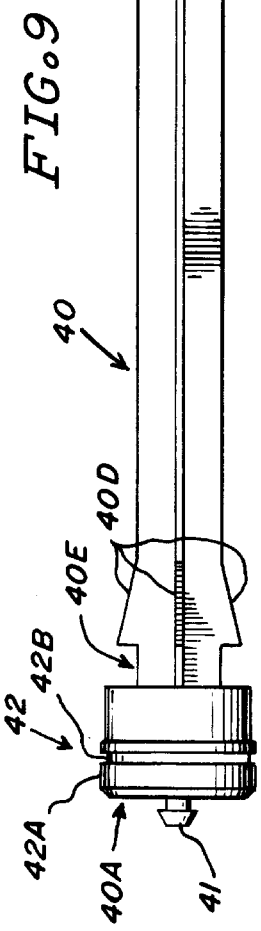
FIG. 7  FIG. 8A  FIG. 8  FIG. 9

SAFETY SYRINGE WITH RETRACTABLE NEEDLE HOLDER

BACKGROUND OF THE INVENTION

This invention relates to disposable syringes having an arrangement which will shield the syringe needle after the syringe has been used so as to thus prevent the sticking or pricking of a human person handling the syringe. The needle stick hazard is a well known health hazzard, regard being given to the possibility of transmitting infectious diseases such as the HIV virus, hepatitis, and the like through needles which have become contaminated through prior use.

Various prior art arrangements have been proposed. Representative examples of prior art arrangements are the Chul 5,256,151, Haining 5,342,323 and Gloyer et al 4,747,830 and the several prior art references cited in these patents.

While a number of prior art arrangements have been proposed, none are as advantageous as the present invention.

SUMMARY OF THE INVENTION

The present invention provides a safety syringe comprising a cylindrical hollow barrel member of semi-elastic material. The barrel has an inner cylindrical surface having a preselected normal or unstretched inner diameter and distal and proximal open ends. A first restraining stop is provided in the barrel projecting radially inwardly a preselected distance from said inner cylindrical surface and being axially spaced a preselected distance from the distal open end of the barrel. The barrel further has a seal and stop means at the distal open end which projects radially inwardly a preselected distance from the inner surface.

The cylindrical hollow barrel member may also include first anti-rotation means positioned between said first restraining stop means and said seal and stop means.

The syringe further includes a cylindrically shaped needle carrier having distal and proximal ends and being positioned initially within the barrel between the first restraining stop means and the seal and stop means. The needle carrier has at the distal end thereof means for receiving and holding an elongated hollow needle means. The needle carrier also has a centrally located hollow longitudinally extending bore throughout. In addition the needle carrier has, at the proximal end thereof, a centrally located female recess means for receiving and holding or retaining a piston extension means. Finally the needle carrier may also include a second anti-rotation means on the outer circumferential surface thereof for engagement with the first anti-rotation means on the barrel so as to prevent rotation of said needle carrier relative to the barrel member.

The syringe further includes an elongated piston rod means having a distal end adapted to be positioned in the barrel member by insertion through the open proximal end thereof. At the distal end of the piston rod is a piston means having a diameter preselected so as to snugly contact the normal unstretched inner cylindrical surface of the barrel member. At the distal end of the piston means is a male-like piston extension means centrally positioned and extending axially a preselected distance and having locking means for engagement with and retention by the female recess means of said needle carrier.

The syringe may also include a piston rod limit means which functions to limit the extent of removal of the piston rod from the barrel member. In the preferred embodiment, this includes a flange means extending radially outward from the barrel member at the proximal open end thereof; and a U-shaped member of resilient material attached at the bight portion thereof to the flange means and having a pair of opposed spaced fingers which straddle the piston rod at the proximal open end of the barrel member. The locking arrangement further includes notch means on the piston rod positioned at a preselected location between the proximal end of the piston means and the proximal end of the piston rod, the aforesaid opposed spaced fingers of the U-shaped member snapping into said notch as the piston rod is removed from the barrel member.

Prior art syringes have had several disadvantages. One disadvantage is that, in some cases, connecting a hollow needle means to the needle carrier could tend to cause rotation of the needle carrier within the barrel of the syringe and could cause unseating of the needle carrier with respect to the distal end of the barrel to thus permit fluid leakage. In the present invention the needle carrier is not held in place with respect to the barrel by means of threads, such as threaded surfaces used in many prior art safety syringes; therefore, the present invention is not prone to that problem. Furthermore, the present invention may include cooperating anti-rotation means on the circumferential surface of the needle carrier and the inner wall of the barrel member so as to prevent relative rotation therebetween.

In the present invention the needle carrier is initially positioned within the barrel member between the first restraining stop means and the seal and stop means, this positioning being firm and positive so that an attached elongated hollow needle means may be effectively administered to a body part. Fluid within the barrel may be injected into the body part by movement of the piston rod means within the barrel in the distal direction. Once all of the fluid has been so administered, then additional movement of the piston in the distal direction will cause engagement between the male member on the distal face of the piston with the female recess in the proximal end of the needle carrier; this final movement of the piston in the distal direction is permitted by the piston engaging the first restraining stop means of the barrel member and stretching the barrel in that region of the barrel from the normal unstretched inner diameter to a somewhat larger diameter so as to permit the distal face of the piston to engage or contact the proximal face of the needle carrier. Thereafter, the piston rod means with the attached needle carrier may be moved longitudinally within the syringe barrel member toward the proximal end of the barrel. The invention is characterized so that the aforesaid movement of the piston means with the attached needle carrier is sufficient so that an elongated hollow needle means attached to the needle carrier would be drawn totally within the barrel member to thus prevent accidental contact of the needle means with an errant human body part.

The optional piston rod movement limit means may be employed to hold the piston rod means in the "safe position".

DESCRIPTION OF THE DRAWINGS

FIG. 1 is an isometric exploded view of the preferred embodiment of the invention.

FIG. 2 shows a partial longitudinal cross-section of the syringe shown in FIG. 1 with the needle carrier positioned within the barrel member between a first restraining stop means and a seal and stop means and with the piston means positioned within the barrel member but spaced axially or longitudinally away from the first restraining stop means.

FIG. 3 is a view similar to FIG. 2 except the piston rod means with attached piston means has been moved completely in the distal direction with the piston means engaging the first restraining stop means and forcing it outwardly, thus stretching the barrel member from its normal unstretched inner diameter to a larger diameter and with the male extension on the piston means engaging the female recess in the needle carrier.

FIG. 4 is a view of the apparatus shown in FIG. 2 as shown along section lines 4—4.

FIG. 5 is another longitudinal cross-section of the device shown in FIG. 1 after the piston rod means has withdrawn the needle carrier with attached elongated hollow needle means and the piston rod means has been locked with respect to any further longitudinal relative movement with the barrel means.

FIG. 6 shows the apparatus shown in FIG. 5 as viewed along section lines 6—6.

FIG. 7 is a longitudinal cross-section of the barrel member.

FIG. 8 is a longitudinal cross-section of the needle carrier.

FIG. 8A is a view of the proximal end of the needle carrier as viewed along section lines 8A—8A.

FIG. 9 is a longitudinal view of the piston rod means.

FIG. 10 shows an alternate embodiment of the invention.

DETAILED DESCRIPTION OF THE INVENTION

In FIG. 1 reference numeral 10 designates a safety syringe with the various components depicted in exploded fashion. The components include a barrel member 20, a needle carrier 30, a piston rod means 40, an elongated hollow needle means 50 and a locking means 60.

The barrel member 20 is shown in larger scale in FIG. 7; it is depicted as a cylindrical hollow barrel member of semi-elastic material such as a plastic well known to those skilled in the art and adapted to contain a fluid. The barrel member has an inner cylindrical surface 20A having a preselected normal or unstretched inner diameter and distal and proximal open ends 20B and 20C respectively. The barrel member further includes a first restraining stop means 21 comprising an inwardly extending shoulder which projects radially inwardly a preselected distance from said inner surface 20A and is axially spaced a preselected distance from the distal open end 20B; the stop means is shown with a sloped or beveled proximal surface 21A and with an inner circumferential surface 21B.

The barrel member further includes a seal and stop means at the distal end 20B identified by reference numeral 22. More specifically the seal and stop means comprises a radially inwardly extending shoulder 22B having at the proximal end thereof an annular axially extending seal 22B. Other seal means such as an "O"-ring may be used in place of seal 22B.

In the preferred embodiment of the invention the barrel member further includes first anti-rotation means positioned between the first restraining stop means and the seal and stop means 21 and 22 respectively. The first anti-rotation means comprises a protrusion shown as a longitudinally extending rib 23 (see also FIG. 4) which extends inwardly from the inner surface 20A of the barrel member.

The barrel member further includes a flange means 24 at the proximal end 20C of the barrel.

The needle carrier 30 is best shown in FIGS. 8 and 8A; it has a cylindrical shape having an outer circumferential surface 30A having a diameter essentially the same as the inside diameter of the barrel member 20. The needle carrier has distal and proximal ends 30B and 30C respectively and a hollow longitudinally extending centrally located bore 30D throughout. At the distal end 30B the needle carrier has a means 30E for receiving and holding an elongated hollow needle means. Those skilled in the art will recognize that different needle receiving and holding means may be used; the arrangement depicted has an axial extension with internal threads for receiving a luer-type elongated hollow needle means. A conically-shaped extension 30F extends in the distal direction from the threaded hub 30E; elements 30E and 30F collectively providing an appropriate support for a needle means 50 shown in FIGS. 1–3 and 5.

At the proximal end 30C of the needle carrier is centrally located a female recess means 31 for receiving and holding a male piston extension means 41. The female recess 31 is centrally positioned and comprises a short bore 31A of a first preselected diameter which opens into a larger diameter recess portion 31B as is clearly shown in FIGS. 2 and 8.

The needle carrier further has second anti-rotation means on the outer surface thereof for engagement with the first anti-rotation means or protrusion 23 which is integral with the barrel member 20. More specifically, the second anti-rotation means on the needle carrier is a longitudinally extending recess 33 shown in FIG. 8A. Those skilled in the art will understand that other anti-rotation means may be used.

As shown in FIG. 2, the needle carrier 30 is positioned initially within the barrel member between the first restraining stop means 21 and the seal and stop means 22. The axial surface 30G (see FIG. 8) at the distal end of the needle carrier abutting the annular seal 22A at the distal end 20B of the barrel.

The elongated piston rod means 40 is shown in detail in FIGS. 6 and 9; it has a distal end 40A and proximal end 40B and an elongated body or rod portion 40C which may have a variety of cross-sections but, in the preferred embodiment, has a cruciform-shape as shown in FIG. 6. At the distal end 40A is a piston means 42 which includes a piston 42A having a diameter preselected so as to snugly contact the normal unstretched inner cylindrical surface 20A of the barrel member 20. A beveled circumferencial surface 42A' is provided on the distal face of the piston means 42. An O-ring recess 42B for receiving an O-ring 42B', as shown in FIG. 3, may also be provided on the circumferential surface of piston 42A, as is well understood by those skilled in the art. As shown in FIG. 9, the elongated rod portion 40C (having the cruciform cross-section) has a uniform dimension except for an outer ramp or incline surface portion 40D terminating close to but spaced from the piston means 42 so as to define a notch 40E therebetween. At the extreme proximal end of the rod portion 40C is an end piece or cap 44.

At the distal end of the piston rod means is a piston extension means 41 which may also be termed the male portion of a locking means so as to provide engagement with and retention by the female recess 31 in the proximal end of the needle carrier 30. Referring to FIGS. 2 and 9, it will be seen that the male extension 41 comprises portions 41A and 41B which are shaped and dimensioned so as to compliment the recesses 31B and 31A respectively of the recess 31 in the needle carrier. The material selected for those portions of the plunger and needle carrier which provide the interlocking action as aforesaid are those well known to those skilled in the art such as resilient plastic.

The piston rod movement limit means 60 is best shown in FIG. 6; it comprises a U-shaped member of resilient material such as plastic attached at its bight portion 60A to the flange means 24 of the barrel by use of an appropriate pin or rivet means 61 having heads or ends 61A and 61B as shown in FIG. 2. The U-shaped member 60 further includes a pair of opposed spaced fingers 60B and 60C which straddle the piston rod 40C at the proximal open end 20C of the barrel member. As indicated, the member 61 is made of a resilient material so that the fingers 60B and 60C maintain contact with the piston rod 40C as the piston rod moves longitudinally with respect to the barrel member 20. Thus, as the piston rod means 40 is moved out of the barrel member the resilient fingers 60B and 60C will eventually contact the inclined portions 40C and 40D of the piston rod and yield enough so as to permit a slight amount of additional movement of the piston rod to the point depicted in FIG. 5 wherein the fingers 60B and 60C are shown in the notch 40E to thereby lock the piston rod with respect to the barrel member.

OPERATION

In use, as aforesaid, the needle carrier is initially positioned between the first restraining stop means 21 and the seal and stop means 22 and the rib 23 of the barrel is in engagement with the recess 33 of the needle carrier. The distal end 40A of the piston rod means 40 is positioned in the barrel member by insertion through the open proximal end 20C thereof. The piston rod movement limit means 60 may be attached to the flange 24 if the locking function is desired. Typically the limit means 60 would be attached to the flange prior to the insertion of the piston, the resilient fingers 60B and 60C to be spread permitting the insertion of the piston rod means.

Once the syringe is in the hands of a professional, a needle means 50 of appropriate size would be attached to the needle carrier, as shown, and then the syringe may be used to administer medications or other fluids to a body. Thus fluid may be drawn into the barrel by relative movement of the piston toward the proximal end 20C of the barrel member following which, when the piston is moved axially toward the distal end 20B of the barrel member, such fluid is forced through the bore 30D of the needle carrier and through the hollow needle means 50. The fluid flow continues until the male locking means 41 is in engagement with the female recess 31. The locking function is facilitated by the beveled surface 42A' on distal face of the piston means 42 engaging the sloped or beveled surface 21A of the first restraining stop means 21. As additional force is applied to the piston rod, the barrel is stretched outwardly to a new diameter Y as shown in FIG. 3 from the original diameter X, also shown in FIG. 3 to thus unlock the needle carrier from its initial position.

FIG. 3 shows the engaged and locked piston rod means and needle carrier; it is clear that the now assembled piston rod means and needle carrier with attached needle may be withdrawn in the proximal direction with respect to the barrel member 20 to a position such as shown in FIG. 5 wherein the needle carrier with assembled needle 50 is totally withdrawn within the barrel member and, as aforesaid, the limit means fingers 60B and 60C are lying within the notch means 40E of the piston rod so as to prevent any further relative axial or longitudinal movement between the needle carrier and the barrel member. The needle means 50, which may be contaminated, is thus safely within the protective barrel 20 where accidental contact of the needle with an errant human body part is prevented.

FIG. 10 shows an alternate arrangement of the invention. Instead of using the limit means 60, the piston rod means of FIG. 10, identified by reference numeral 140, has a cruciform cross-section 140C adapted to be broken off as at 140C' after completion of the use of the syringe for its intended purpose and subsequent withdrawal of the needle within the barrel member as aforesaid.

While I have described a preferred embodiment of the invention, it will be understood that the invention is limited only by the scope of the following claims:

The embodiments of an invention in which an exclusive property or right is claimed are defined as follows:

1. A safety syringe comprising:
   (a) a cylindrical hollow barrel member of semi-elastic material adapted to contain a fluid, having a preselected normal unstretched inner cylindrical surface defined by an inner diameter and distal and proximal open ends, and said barrel member further comprising:
      (i) a first restraining stop means projecting radially inwardly a preselected distance from said inner cylindrical surface and axially spaced a preselected distance from said distal open end;
      (ii) a seal and stop means at said distal open end projecting radially inwardly a preselected distance from said inner cylindrical surface;
      (iii) first anti-rotation means positioned between said first restraining stop means and said seal and stop means, and
      (iv) flange means extending radially outward at said proximal open end;
   (b) a cylindrical shaped needle carrier having distal and proximal ends and being positioned initially within said barrel member between said first restraining stop means and said seal and stop means, said needle carrier being further characterized by having:
      (i) at said distal end thereof means for receiving and holding an elongated hollow needle means;
      (ii) a hollow longitudinally-extending bore throughout;
      (iii) at said proximal end thereof centrally located female recess means for receiving and holding piston extension means; and
      (iv) second anti-rotation means on the outer surface thereof for engagement with said first anti-rotation means to prevent rotation of said needle carrier relative to said barrel member,
   (c) an elongated piston rod means having a distal end adapted to be positioned in said barrel member by insertion through said open proximal end thereof and having at the distal end thereof a piston means having a diameter preselected so as to snugly contact said preselected normal unstretched inner cylindrical surface of said barrel member, said piston rod means further comprising:
      (i) piston extension means centrally positioned on the distal end of said piston means extending axially a preselected distance, and having locking means for engagement with and retention by said recess means of said needle carrier; and
      (ii) notch means on said piston rod means positioned at a preselected location between the proximal end of said piston means and a proximal end of said piston rod means; and
   (d) piston rod movement limit means attached to said flange means, adapted to engage said piston rod means and to engage said notch means, upon partial withdrawal of said piston rod means from said barrel member, to thereby lock said piston rod to said barrel member;

whereby said syringe is further characterized by said piston means, when moved axially within and toward said distal end of said barrel member, forcing fluid through said bore until contact therewith said first restraining stop means, said piston means and said first restraining stop means having co-acting means which function, upon further axial movement of said piston means toward the distal end of said barrel member, to force outward said first restraining stop means and the adjacent section of said barrel member to permit the engagement of and attachment to said piston extension means with said recess means of said needle carrier, following which said piston rod means with attached needle carrier may be moved in unison longitudinally toward said proximal end of said barrel member sufficiently so that an elongated hollow needle means attached to said needle carrier would be entirely within said barrel member to thus prevent accidental contact of said needle means with an errant body part; and whereby said limit means would then be in engagement with said notch means to lock said piston rod means to said barrel means to thus prevent further relative axial movement of said piston rod means and said barrel means.

2. Apparatus of claim 1 further characterized by (i) said seal and stop means including an annular seal located on a proximal portion thereof, and (ii) said needle carrier, at said distal end thereof, having a planar surface positioned to engage said annular seal.

3. Apparatus of claim 1 further characterized by said coacting means of said piston means and said first restraining stop means comprising beveled surface means.

4. Apparatus of claim 1 further characterized by said needle carrier centrally located female recess means having (i) a first portion of a preselected diameter adjacent to said proximal end of said needle carrier, and (ii) a second portion adjacent to and of a larger diameter than said first portion.

5. Apparatus of claim 4 further characterized by said locking means of said piston extension means having a male shape complimentary to said needle carrier female recess means.

6. Apparatus of claim 1 further characterized by said piston rod movement limit means comprising a U-shaped member having a bight portion and attached at said bight portion to said flange means and having a pair of opposed spaced resilient fingers straddling said piston rod means at said proximal open end of said barrel member.

7. Apparatus of claim 1 further characterized by said first and second anti-rotation means comprising complementary axially extending protrusion and recess means.

8. Apparatus of claim 7 further characterized by said needle carrier having a recess and said barrel member having a rib.

9. A safety syringe comprising:
(a) a cylindrical hollow barrel member of semi-elastic material adapted to contain a fluid having a preselected normal unstretched inner cylindrical surface defined by an inner diameter and distal and proximal open ends, and said barrel member further comprising:
   (i) a first restraining stop means projecting radially inwardly a preselected distance from said inner cylindrical surface and axially spaced a preselected distance from said distal open end;
   (ii) a seal and stop means at said distal open end projecting radially inwardly a preselected distance from said inner cylindrical surface; and
   (iii) first anti-rotation means positioned between said first restraining stop means and said seal and stop means, (b) a cylindrical shaped needle carrier having distal and proximal ends and being positioned initially within said barrel member between said first restraining stop means and said seal and stop means, said needle carrier being further characterized by having:
   (i) at said distal end thereof means for receiving and holding an elongated hollow needle means;
   (ii) a hollow longitudinally-extending bore throughout;
   (iii) at said proximal end thereof centrally located recess means for receiving and holding piston extension means; and
   (iv) second anti-rotation means on the outer surface thereof for engagement with said first anti-rotation means to prevent rotation of said needle carrier relative to said barrel member; and (c) an elongated piston rod means having a distal end adapted to be positioned in said barrel member by insertion through said open proximal end thereof and having at the distal end thereof a piston means having a diameter preselected so as to snugly contact said preselected normal unstretched inner cylindrical surface of said barrel member, said piston rod means further comprising piston extension means centrally positioned on the distal end of said piston means extending axially a preselected distance, and having locking means for engagement with and retention by said recess means of said needle carrier; and whereby said syringe is further characterized by said piston means when moved axially within and toward said distal end of said barrel member, forcing fluid through said bore until contact therewith said first restraining stop means, said piston means and said first restraining stop means having co-acting means which function, upon further axial movement of said piston means toward the distal end of said barrel member, to force outward said first restraining stop means and the adjacent section of said barrel means to permit the engagement of and attachment to said piston extension means with said recess means of said needle carrier, following which said piston rod means with attached needle carrier may be moved in unison longitudinally toward said proximal end of said barrel member sufficiently so that an elongated hollow needle means attached to said needle carrier would be entirely within said barrel member to thus prevent accidental contact of said needle means with an errant body part.

10. A safety syringe comprising:
a) a cylindrical hollow barrel member of semi-elastic material adapted to contain a fluid having a preselected normal unstretched inner cylindrical surface defined by an inner diameter and distal and proximal open ends, and said barrel member further comprising:
   (i) a first restraining stop means projecting radially inwardly a preselected distance from said inner cylindrical surface and axially spaced a preselected distance from said distal open end; and
   (ii) a seal and stop means at said distal open end projecting radially inwardly a preselected distance from said inner cylindrical surface;
b) a cylindrical shaped needle carrier having distal and proximal ends and being positioned initially within said barrel member between said first restraining stop means and said seal and stop means, said needle carrier being further characterized by having:
   (i) at said distal end thereof means for receiving and holding an elongated hollow needle means;
   (ii) a hollow longitudinally-extending bore throughout; and (iii) at said proximal end thereof centrally located recess means for receiving and holding piston extension means; and c) an elongated piston rod means having a distal end adapted to be positioned in said barrel member by insertion through said open proximal end thereof and having at the distal end thereof a piston means having a diameter preselected so as to snugly contact said preselected normal unstretched inner cylindrical surface of said barrel member, said piston rod means further comprising: piston extension means centrally positioned on the distal end of said piston means extending axially a preselected distance, and having locking means for engagement with and retention by said recess means of said needle carrier; and whereby said syringe is further characterized by said piston means, when moved axially within and toward said distal end of said barrel member, forcing fluid through said bore until contact therewith said first restraining stop means, said piston means and said first restraining stop means having co-acting means which function, upon further axial movement of said piston means toward the distal end of said barrel member, to force outward said first restraining stop means and the adjacent section of said barrel member to permit the engagement of and attachment to said piston extension means with said recess means of said needle carrier, following which said piston rod means with attached needle carrier may be moved in unison longitudinally toward said proximal end of said barrel member sufficiently so that an elongated hollow needle means attached to said needle carrier would be entirely within said barrel member to thus prevent accidental contact of said needle means of an errant body part.

* * * * *